United States Patent [19]

Reusser

[11] 4,332,898
[45] Jun. 1, 1982

[54] HYBRID PLASMID AND PROCESS OF MAKING SAME

[75] Inventor: Fritz Reusser, Portage, Mich.

[73] Assignee: The Upjohn Company, Kalamazoo, Mich.

[21] Appl. No.: 159,852

[22] Filed: Jun. 16, 1980

Related U.S. Application Data

[63] Continuation-in-part of Ser. No. 152,347, May 22, 1980, abandoned.

[51] Int. Cl.³ .............................................. C12N 15/00
[52] U.S. Cl. .................................... 435/172; 435/253; 435/317; 435/849
[58] Field of Search ........................ 435/317, 172, 253

[56] References Cited
PUBLICATIONS

Bolivar et al., Gene, 2 pp. 95–113 (1977).
Chakrabarty, Genetic Engineering, CRC Press Inc., pp. 83–111 (1978).

Primary Examiner—Alvin E. Tanenholtz
Attorney, Agent, or Firm—Roman Saliwanchik

[57] ABSTRACT

A novel chemical compound, plasmid pUC1021, which was constructed from *Bacillus megaterium* chromosomal DNA and plasmid pBR322. Hybrid plasmid pUC1021 contains a functional tet gene promoter, and, thus, is useful as a cloning vehicle in recombinant DNA work. For example, using well known DNA methodology, a desired gene, for example, the insulin gene, can be inserted into pUC1021 and the resulting plasmid can then be transformed into a suitable host microbe which, upon culturing, produces the desired insulin.

6 Claims, 1 Drawing Figure

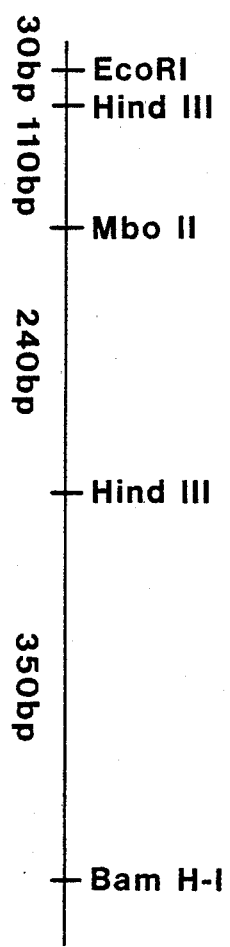

HYBRID PLASMID AND PROCESS OF MAKING SAME

CROSS REFERENCE TO RELATED APPLICATION

This is a continuation-in-part of my copending application Ser. No. 152,347, filed on May 22, 1980 and now abandoned.

BACKGROUND OF THE INVENTION

The development of plasmid vectors useful for recombinant DNA genetics among microorganisms is well known. The editorial in Science, Vol. 196, April 1977, gives a good summary of DNA research. This editorial is accompanied by a number of supporting papers in the same issue of Science.

Similar DNA work is currently being done on industrially important microorganisms of the genus Streptomyces. [Bibb, M. J., Ward, J. M., and Hopwood, D. A. 1978. "Transformation of plasmid DNA into Streptomyces at high frequency."Nature 274, 398–400.]- Though plasmid DNA's have been detected in several streptomycetes [Huber, M. L. B. and Godfrey, O. 1978. "A general method for lysis of Streptomyces species." Can. J. Microbiol. 24, 631–632.] [Schrempf, H., Bujard, H., Hopwood, D. A. and Goebel, W. 1975. "Isolation of covalently closed circular deoxyribonucleic acid from *Streptomyces coelicolor* A3(2)." J. Bacteriol. 121, 416–421.] [Umezawa, H. 1977. "Microbial secondary metabolites with potential use in cancer treatment (Plasmid involvement in biosynthesis and compounds)." Biomedicine 26, 236–249.], [Malik, V. S. 1977. Preparative Method for the isolation of supercoiled DNA from a chloramphenicol producing streptomycete. J. Antibiotics 30, 897–899.], only one streptomycete plasmid has been physically isolated and extensively characterized in the literature [Schrempf, supra]. The existence of other plasmids in the genus Streptomyces has been inferred from reported genetic data as follows:

(1) Akagawa, H., Okanishi, M. and Umezawa, H. 1975. "A plasmid involved in chloramphenicol production in *Streptomyces venezuelae*: Evidence from genetic mapping." J. Gen. Microbiol. 90, 336–346.

(2) Freeman, R. F. and Hopwood, D. A. 1978. "Unstable naturally occurring resistance to antibiotics in Streptomyces." J. Gen. Microbiol. 106, 377–381.

(3) Friend, E. J., Warren, M. and Hopwood, D. A. 1978. "Genetic evidence for a plasmid controlling fertility in an industrial strain of *Streptomyces rimosus*." J. Gen. Microbiol. 106, 201–206.

(4) Hopwood, D. A. and Wright, H. M. 1973. "A plasmid of *Streptomyces coelicolor* carrying a chromosomal locus and its inter-specific transfer." J. Gen. Microbiol. 79, 331–342.

(5) Hotta, K., Okami, Y. and Umezawa, H. 1977. "Elimination of the ability of a kanamycin-producing strain to biosynthesize deoxystreptamine moiety by acriflavine." J. Antibiotics 30, 1146–1149.

(6) Kirby, R., Wright, L. F. and Hopwood, D. A. 1975. "Plasmid-determined antibiotic synthesis and resistance in *Streptomyces coelicolor*." Nature 254, 265–267.

(7) Kirby, R. and Hopwood, D. A. 1977. "Genetic determination of methylenomycin synthesis by the SCPI plasmid of *Streptomyces coelicolor* A3(2)." J. Gen. Microbiol. 98, 239–252.

(8) Okanishi, M., Ohta, T. and Umezawa, H. 1969. "Possible control of formation of aerial mycelium and antibiotic production in Streptomyces by episomic factors." J. Antibiotics 33, 45–47.

Plasmid pBR322 is a well known plasmid which can be obtained from *E. coli* RR1, NRRL B-12014. The restriction endonuclease map for pBR322 is published; Sutcliff, J. G. "pBR322 restriction map derived from the DNA sequence: accurate DNA size markers up to 4361 nucleotide pairs long." Nucleic Acids Research 5, 2721–2728, 1978. This map is incorporated herein by reference to the above publication.

BRIEF SUMMARY OF THE INVENTION

Plasmid pUC1021 is constructed from *Bacillus megaterium*, NRRL B-12165 chromosomal DNA and plasmid pBR322. Thus, hybrid plasmid pUC1021 contains a functional tet gene promoter region composed of *B. megaterium* DNA and pBR322 DNA.

The inserted *B. megaterium* DNA was mapped for restriction enzyme sites, and the DNA base sequence was determined for the first 50–60 bases from each end of the insert. The sequencing results show that the promoter region is purine-rich and contains three A-clusters.

pUC1021 is useful as a cloning vector in DNA work wherein desired genes are incorporated into the chimeric plasmid, and the resulting plasmid then transformed into a suitable host.

REFERENCE TO THE DRAWING

Restriction enzyme map for the *B. megaterium*-pBR322 promoter region. The inserted *B. megaterium* segment is located between the two HindIII sites.

Following is the DNA sequence of *B. megaterium*-pBR322 promoter region. The *B. megaterium* insert is located between the two HindIII sites and the *B. megaterium* promoter region is underlined.

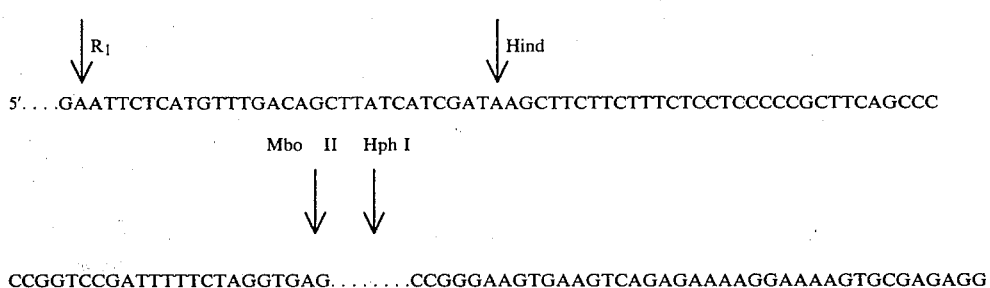

↓ Hind

GAAGGAAAAAGAGGGGAAGCTTTAATGCGGTAGTTTATCACAGTTAAATTGCTAACGCAGTCAGGCACCG

TGTATGAAATC....3' pUC1021 can be used to create recombinant plasmids which can be introduced into host bacteria by transformation. The process of creating recombinant plasmids is well known in the art. Such a process comprises cleaving the isolated vector plasmid, e.g. pUC1021, at specific sites by means of restriction endonucleases, for example, MboII, HpaII, or HaeIII. The plasmid, which is a circular DNA molecule, is thus converted into linear DNA molecules by the enzymes which cut the two DNA strands at a specific site. Other non-vector DNA is similarly cleaved with the same enzyme(s). Upon mixing the linear vector or portions thereof and non-vector DNA's, their single-stranded or blunt ends can pair with each other, and in the presence of a second enzyme known as polynucleotide ligase can be covalently joined to form a single circle of DNA.

The above procedure also can be used to insert a length of DNA from any plant or animal into pUC1021. For example, the DNA which codes for ribosomal RNA in the frog can be mixed with pUC1021 DNA that has been cleaved. The resulting circular DNA molecules consist of plasmid pUC1021 with an inserted length of frog rDNA.

The recombinant plasmids containing a desired genetic element, prepared by using pUC1021, can be introduced into a host organism for expression. Examples of valuable genes which can be inserted into host organisms by the above described process are genes coding for somatostatin, rat proinsulin, and proteases.

DETAILED DESCRIPTION OF THE INVENTION

The Microorganisms and Plasmids

The following microorganisms are available from the permanent collection of the Northern Regional Research Laboratory, U.S. Department of Agriculture, Peoria, IL, U.S.A.

NRRL B-11371: *E. coli* HB101
NRRL B-12014: *E. coli* RR1 (pBR322)
NRRL B-12165: *B. megaterium*
NRRL B-12167: *E. coli* HB101 (pUC1021)

These deposits are available to the public upon the grant of a patent to the assignee, The Upjohn Company, disclosing them. The deposits are also available as required by foreign patent laws in countries wherein counterparts of the subject application, or its progeny, are filed. However, it should be understood that the availabiltiy of a deposit does not constitute a license to practice the subject invention in derogation of patent rights granted by governmental action.

The following examples are illustrative of the process and products of the subject invention but are not to be construed as limiting. All percentages are by weight and all solvent mixture proportions are by volume unless otherwise noted.

EXAMPLE 1

Isolation of Vector pBR322 DNA from *E. coli* NRRL B-12014

A 100 ml. culture of *E. coli* RR1 (pBR322) is grown overnight in L-broth which consists of the following ingredients:

| Bacto tryptone (Difco) | 10 g/liter |
| --- | --- |
| Bacto yeast extract (Difco) | 5 g/liter |
| NaCl | 5 g/liter |
| Ampicillin | 50 mg/liter |

The cells are recovered by centrifugation at 17,000 × g. for 10 minutes in a refrigerated centrifuge. The pellet is suspended in 2.5 ml. 50 mM tris buffer (pH 8) containing 25% sucrose. One-half ml. of lysozyme stock solutin is added (5 mg./ml. in TES buffer). The mixture is allowed to stand in ice for 5 minutes. At this point 1 ml. EDTA (ethylene diamine tetraacetic acid) (0.25 M, pH 8) is added and the mixture is again allowed to stand in ice for 5 minutes. One and a quarter ml. of 5 N NaCl and 1 ml. 10% SDS (sodium dodecyl sulfate) are then added. The mixture is shaken on a Vortex and incubated at 37° C. for 20 minutes. Then 10 μl of ribonuclease A (20 mg./ml.) is added and the sample is again incubated at 37° C. for 20 minutes. The mixture is then kept in ice overnight and then centrifuged at 35,000 × g. for 30 minutes in a refrigerated centrifuge. 2 ml. of the supernatant solution (lysate) are carefully removed with a pipette. Four and one-half ml. of TES buffer (30 mM tris.HCl, pH 8, 5 mM EDTA.Na$_2$, 50 mM NaCl) are mixed with 1.5 ml. EtBr (ethidium bromide) stock (1 mg./ml. in TES buffer) and 7.5 g. solid CsCl. After the salt has dissolved, 2 ml. of the lysate, described above, is added and the mixture is transferred into a polyallomer tube fitting a titanium 50 (Ti 50) head (Beckman ultracentrifuge). The tubes are filled to the top with mineral oil and centrifuged in a Beckman ultracentrifuge at 40,000 rpm in a Ti 50 head at 20° C. for at least 2 days. The DNA is located under a long wave UV-lamp and the heavier band containing the plasmid DNA is removed with a syringe by puncturing the tube wall from the side. The samples are extensively dialysed against 100 volumes of TES buffer at 4° C. Following dialysis 1/10 sample volume of a 3 M NaAcetate stock solution is added and the plasmid DNA is precipitated by the addition of 2 volumes of cold ethanol. The resulting pellet is then lyophilized and redissolved in 200 μl 10 mM tris buffer, pH 7.8 containing 1 mM EDTA.Na$_2$ and frozen for storage.

EXAMPLE 2

Isolation of Chromosomal DNA from *B. megaterium* NRRL B-12165.

By substituting *B. megaterium* NRRL B-12165 for *E. coli* NRRL B-12014 in Example 1, there is obtained DNA from *B. megaterium*.

EXAMPLE 3

Preparation of Hybrid Plasmid pUC1021.

Plasmid pBR322 DNA is digested with HindIII restriction enzyme by mixing 4 μl of DNA (0.3 μg/μl), 11 μl DD.H₂O (double distilled water), 2 μl 10x high salt restriction buffer (Post, L. E., Arfsten, A. E., Reusser, F. and Nomura, M. 1978. DNA sequences of promoter regions for the str and spc ribosomal protein operons in *E. coli*. Cell 15, 215-229) and 1.5 μl of HindIII solution. This mixture is incubated at 37° C. for 1 hr. Five μl of bacterial alkaline phosphatase (BAP.F, Worthington) is then added and the mixture is incubated at 65° C. for 10 minutes. Following the nuclease treatment, 350 μl of 10 mM Tris-acetate, pH 7.8, and 40 μl of 3M Na.acetate stock solution are added. The sample is extracted three times with an equal volume of phenol, precipitated with ethanol, lyophilized and redissolved in 10 mM tris buffer. This solution is used for the ligation reaction described below.

*B. megaterium* DNA is subjected to HindIII digestion in a reaction mixture containing 10 μl *B. megaterium* DNA (0.5 μg/μl), 6 μl DD.H₂O, 2 μl 10x high salt restriction buffer and 2 μl HindIII solution. This mixture is kept at 37° C. for 1 hour. The reaction is stopped by incubating the sample at 65° C. for 10 minutes. The solution is then used for the ligation reaction.

For ligation 10 μl pBR322 digestion mix, 20 μl *B. megaterium* digestion mix, and 30 μl DD.H₂O are combined. Ten μl 0.5 M Tris.HCl, pH 7.8, 20 μl 100 mM DDT (dithiothreitol), 10 μl 100 mM MgCl₂, and 10 μl 10 mM ATP (adenosine triphosphate) are mixed separately and then combined with the digested DNA mixture. Finally 1.5 μ of T₄ ligase is added and the sample is kept in ice for 1-2 days. Following ligation, the solution is adjusted to 0.3 M with Na.acetate and the DNA precipitated with ethanol. The pellet is washed in ethanol and lyophilized. The essentially pure hybrid plasmid pUC1021, thus obtained, is redissolved in 200 μl transformation buffer containing 10 mM Tris.HCl, pH 7, 10 mM CaCl₂ and 10 mM MgCl₂.

For transformation into *E. coli* HB101, seed is grown overnight in L-broth and diluted 1:100 into fresh L-broth the next day. The cells are incubated at 37° C. and allowed to grow to an OD₆₀₀ of 0.6. At this point 50 ml. of culture is centrifuged in the cold, the pellet resuspended in 25 ml. cold 10 mM MgSO₄ and centrifuged again. The pellet is then resuspended in 25 ml. cold 50 mM CaCl₂ solution and kept on ice for 20 minutes. After centrifugation the cells are resuspended in 5 ml. cold 50 mM CaCl₂ solution. One hundred μl of ligase mixture (see above) is mixed with 200 μl cell suspension. This mixture is kept in ice for 15 minutes, heated to 42° C. for 2 minutes and then left at room temperature for 10 minutes. Ten μl aliquots are plated on freshly prepared agar plates containing 25 ml. of L-broth, 1.5% agar and 50 μg of ampicillin/ml. Colonies are selected and scored for tetracycline resistance.

Colonies are screened for the presence of plasmids of different sizes by making a small amount of cleared lysate. Single colonies are grown in small cultures overnight. A 1 ml. culture is centrifuged for 2 minutes in an Eppendorf microcentrifuge. The pellet is resuspended in 25 μl 25% sucrose in 50 mM Tris.HCl, pH 8.0. Five μl of a lysozyme solution (5 mg./ml. in 10 mM Tris.HCl, pH 8.0) is added. After 5 minutes at 0° C., 10 μl 0.25 M EDTA, pH 7.0 is added. After an additional 5 minutes incubation at 0° C., 12.5 μl 5 M NaCl and 5 μl 10% SDS are added, and the mixture is quickly shaken by a Vortex mixer. After 1-2 hours at 0° C., the mixture is centrifuged 5 minutes in an Eppendorf microcentrifuge and 20 μl supernatant is analyzed using agarose slab gel electrophoresis. Detection of plasmid DNA and estimation of its approximate size are made by examining gels stained with ethidium bromide under a long-wave ultraviolet lamp.

Suspected transformants are then grown in 10 ml. cultures. Cleared lysates are prepared as described above. The supernatants are treated with pancreatic RNase A (25 mg./ml., 30 minutes at room temperature), and then extracted with phenol. DNA is precipitated from the aqueous phase by ethanol, and then digested with suitable restriction enzymes to analyze DNA fragments cloned in the transformants.

Restriction Endonuclease Digestion and Agarose Gel Electrophoresis

Restriction endonucleases were obtained as commercial preparations from Miles Laboratories, Bethesda Research Laboratories. Enzyme digestions were carried out as specified in the publication of Post, L. E., Arfsten, A. E., Reusser, F. and Nomura, M., supra.

The digested samples were applied to 0.7-1% agarose gels and were electrophoresed for 2 hours at a constant applied voltage of 10-15 v/cm of gel height. [Sharp, P. A., Sugden, J. and Sambrook, J. 1973. Detection of two restriction endonuclease activities in *Haemophilus parainfluenzae* using analytical agarose-ethidium bromide electrophoresis. Biochemistry 12, 3055-3063]. The molecular weights of restriction fragments were determined relative to the standard migration patterns of bacteriophage lambda DNA digested with enzyme HindIII [Murray, K. and Murray, N. E. 1975. Phage lambda receptor chromosomes for DNA fragments made with restriction endonuclease III of *Haemophilus influenzae* and restriction endonuclease I of *Escherichia coli*. J. Mol. Biol. 98, 551-564) or EcoRI [Helling, R. B., Goodman, H. M. and Boyer, H. W. 1974. Analysis of endonuclease R.EcoRI fragments of DNA from lambdoid bacteriophages and other viruses by agarose-gel electrophoresis. J. Virology 14, 1235-1244].

Examples of other vectors which can be used in the invention as a substitute for pBR322 are pBR313, which codes for ampicillin and tetracycline resistance, pSC101, which codes for tetracycline resistance, pCR11, which codes for kanamycin resistance, λ bacteriophage vectors, for example, charon phages, and yeast 2μ plasmid DNA.

Examples of other hosts for the vectors are any *E. coli* K-12 derivative [Bacteriological Reviews, Dec. 1972, pages 525-557] (these have been approved by the NIH Guidelines) and yeasts, other fungi, or other bacteria. It is recognized that these latter hosts would also have to be approved by the NIH Guidelines.

Plasmid pUC1021 can be isolated from *E. coli* HB101 transformants by well known procedures, e.g. using the procedure described in Example 1.

The work described herein was all done in conformity with physical and biological containment requirements specified in the NIH Guidelines.

I claim:

1. *E. coli* HB101 (pUC1021) having the deposit accession number NRRL B-12167.

2. Hybrid plasmid pUC1021 characterized as follows:

(a) it is a hybrid plasmid which has the entire nucleotide sequence of plasmid pBR322 and a foreign DNA insert at the HindIII site of pBR322;
(b) said DNA insert, and direction of insertion, being shown by the restriction map in the drawing;
(c) said DNA insert being further characterized by (1) the following partial nucleotide sequence which is located between the two HindIII sites of pUC1021: CCGGGAAGTGAAGTCAGAGAAAAGGAAAAGTGCGAGAGGGAAGGAAAAGAGGGGA;(2) being 350 base pairs in length; and (3) having a single MboII restriction site.

3. A process for preparing hybrid plasmid pUC1021 which comprises:

(a) linearizing plasmid pBR322 with HindIII to obtain linear plasmid DNA;
(b) obtaining chromosomal DNA from *Bacillus megaterium* NRRL B-12165.
(c) digesting said chromosomal DNA with HindIII, and
(d) ligating said digested linear plasmid DNA from pBR322 and said digested chromosomal DNA from *Bacillus megaterium*, NRRL B-12165, to obtain hybrid plasmid pUC1021.

4. A process for cloning plasmid pUC1021 into a suitable host by transformation.

5. A process, according to claim 4, wherein said suitable host is a bacterium.

6. A process, according to claim 5, wherein said bacterium is *E. coli* HB101

* * * * *